US008283320B2

(12) United States Patent
Wolff

(10) Patent No.: US 8,283,320 B2
(45) Date of Patent: *Oct. 9, 2012

(54) HAEMOSTATIC KIT, A METHOD OF PREPARING A HAEMOSTATIC AGENT AND A METHOD OF PROMOTING HAEMOSTASIS

(75) Inventor: Jørgen Wolff, Birkerød (DK)

(73) Assignee: Ferrosan Medical Devices A/S, Soeborg (DK)

(*) Notice: Subject to any disclaimer, the term of this patent is extended or adjusted under 35 U.S.C. 154(b) by 0 days.

This patent is subject to a terminal disclaimer.

(21) Appl. No.: 13/082,109

(22) Filed: Apr. 7, 2011

(65) Prior Publication Data

US 2011/0245867 A1   Oct. 6, 2011

Related U.S. Application Data

(63) Continuation of application No. 10/326,080, filed on Dec. 23, 2002, now Pat. No. 7,923,431.

(60) Provisional application No. 60/367,515, filed on Mar. 27, 2002, provisional application No. 60/341,812, filed on Dec. 21, 2001.

(51) Int. Cl.
*A61K 38/36* (2006.01)
*A61K 38/39* (2006.01)
*A61K 47/48* (2006.01)
*A61P 7/02* (2006.01)
*C07K 14/745* (2006.01)

(52) U.S. Cl. ...................... 514/13.7; 514/17.2
(58) Field of Classification Search .................. None
See application file for complete search history.

(56) References Cited

U.S. PATENT DOCUMENTS

| 2,465,357 A | 3/1949 | Correll |
| 2,465,860 A | 3/1949 | Fleischmann |
| 2,558,395 A | 6/1951 | Studer |
| 3,224,434 A | 12/1965 | Molomut et al. |
| 3,678,933 A | 7/1972 | Moore et al. |
| 3,815,580 A | 6/1974 | Oster |
| 3,869,539 A | 3/1975 | Kring et al. |
| 3,930,052 A | 12/1975 | De Brou et al. |
| 4,098,728 A | 7/1978 | Rosenblatt et al. |
| 4,150,744 A * | 4/1979 | Fennimore ............... 206/205 |
| 4,265,233 A | 5/1981 | Sugitachi |
| 4,280,954 A | 7/1981 | Yannas et al. |
| 4,320,201 A | 3/1982 | Berg et al. |
| 4,492,305 A | 1/1985 | Avery |
| 4,515,637 A | 5/1985 | Cioca |
| 4,522,302 A | 6/1985 | Paikoff |
| 4,557,377 A | 12/1985 | Maloney |
| 4,559,304 A | 12/1985 | Kasai et al. |
| 4,655,211 A | 4/1987 | Sakamoto et al. |
| 4,696,812 A | 9/1987 | Silbering et al. |
| 4,735,616 A | 4/1988 | Eibl et al. |
| 4,749,689 A | 6/1988 | Miyata et al. |
| 4,851,521 A | 7/1989 | Della Valle et al. |
| 4,861,714 A | 8/1989 | Dean, Jr. et al. |
| 4,863,856 A | 9/1989 | Dean, Jr. et al. |
| 4,891,359 A | 1/1990 | Saferstein et al. |
| 4,982,769 A | 1/1991 | Fournier et al. |
| 4,997,753 A | 3/1991 | Dean, Jr. et al. |
| 5,024,841 A | 6/1991 | Chu et al. |
| 5,037,740 A | 8/1991 | Tanaka et al. |
| 5,112,750 A | 5/1992 | Tanaka et al. |
| 5,149,540 A | 9/1992 | Kunihiro et al. |
| 5,180,583 A | 1/1993 | Hedner |
| 5,356,883 A | 10/1994 | Kuo et al. |
| 5,387,208 A | 2/1995 | Ashton et al. |
| 5,394,886 A | 3/1995 | Nabai et al. |
| 5,399,361 A | 3/1995 | Song et al. |
| 5,401,511 A | 3/1995 | Margalit |
| 5,443,481 A | 8/1995 | Lee |
| 5,456,693 A | 10/1995 | Conston et al. |
| 5,462,860 A | 10/1995 | Mach |
| 5,503,848 A | 4/1996 | Perbellini et al. |
| 5,512,301 A | 4/1996 | Song et al. |
| 5,595,735 A | 1/1997 | Saferstein et al. |
| 5,643,596 A | 7/1997 | Pruss et al. |
| 5,645,849 A | 7/1997 | Pruss et al. |
| 5,660,854 A | 8/1997 | Haynes et al. |
| 5,669,934 A | 9/1997 | Sawyer |
| 5,690,675 A | 11/1997 | Sawyer et al. |
| 5,690,954 A | 11/1997 | Illum |

(Continued)

FOREIGN PATENT DOCUMENTS

BG  0051589  7/1993

(Continued)

OTHER PUBLICATIONS

Andrew Raftery, "Absorbable haemostatic materials and intraperitoneal adhesion formation", Br. J. Surg. 67:57-58 (1980).
Branski et al., "Mucosal Wound Healing in a Rabbit Model of Subglottic Stenosis," Arch Otolaryngol Head Neck Surg, vol. 131, Feb. 2005, p. 153-157.
Cantor et al., "Gelfoam® and Thrombin in treatment of massive gastroduodenal hemorrhage—A preliminary report," American Journal of Surgery, Dec. 1950.
Changez et al.; "Efficacy of antibiotics-loaded interpenetrating network (IPNs) hydrogel based on poly (acrylic acid) and gelatin for treatment of experimental osteomyelitis: in vivo study."; Biomaterials; vol. 26, No. 14; 2005; pp. 2095-2104.
Choi et al., "Studies on Gelatin-Based Sponges. Part III: A Comparative Study of Cross-linked Gelatin/Alginate, Gelatin/Hyaluronate and Chitosan/Hyaluronate Sponges and Their Application as a Wound Dressing in Full-Thickness Skin Defect of Rat," J. of Mat. Sci., Mat. In Med., vol. 12, Jan. 2001, pp. 67-73.
De Laco, et al., "Efficacy of a Hyaluronan Derivative gel in postsurgical adhesion prevention in the presence of inadequate hemostasis", Surgery 130(1):60-64 (2001).
Dembo M.A. et al.; "Antiseptic hemostatic preparations, their properties and study."; Lech.Prep. Krovi. Tkanei; 1974; pp. 139-140.
Dodd et al., "Minimally invasive treatment of malignant hepatic tumors. At the threshold of a major breakthrough". Radiographics 2000; 20:9-27.

(Continued)

*Primary Examiner* — Marcela M Cordero Garcia
(74) *Attorney, Agent, or Firm* — Jonathan D. Ball; King & Spalding

(57) ABSTRACT

A haemostatic kit to be used as a medical device provides for a containment unit and a haemostatic agent in said containment unit, said haemostatic agent occupying less than 90% of the volume of the containment unit. This allows for facile and consequently sterile preparation of, for instance, a gelatin paste for use in haemostatis when combined with saline, thrombin or another agent to assist in haemostatis.

19 Claims, 2 Drawing Sheets

U.S. PATENT DOCUMENTS

| | | | |
|---|---|---|---|
| 5,700,476 A | 12/1997 | Rosenthal et al. | |
| 5,712,161 A | 1/1998 | Koezuka et al. | |
| 5,723,308 A | 3/1998 | Mach et al. | |
| 5,743,312 A | 4/1998 | Pfeifer et al. | |
| 5,749,895 A | 5/1998 | Sawyer et al. | |
| 5,791,352 A | 8/1998 | Reich et al. | |
| 5,795,330 A | 8/1998 | Tofighi et al. | |
| 5,798,091 A | 8/1998 | Trevino et al. | |
| 5,823,671 A | 10/1998 | Mitchell et al. | |
| 5,824,015 A | 10/1998 | Sawyer | |
| 5,863,496 A | 1/1999 | McElhany | |
| 5,883,078 A | 3/1999 | Seelich et al. | |
| 5,890,610 A | 4/1999 | Jansen et al. | |
| 5,895,412 A | 4/1999 | Tucker | |
| 5,908,054 A | 6/1999 | Safabash et al. | |
| 5,931,165 A | 8/1999 | Reich et al. | |
| 5,939,259 A | 8/1999 | Harvey et al. | |
| 5,951,531 A | 9/1999 | Ferdman et al. | |
| 5,951,583 A | 9/1999 | Jensen et al. | |
| 5,957,166 A | 9/1999 | Safabash | |
| 5,986,168 A | 11/1999 | Noishiki et al. | |
| 6,007,613 A | 12/1999 | Izoret | |
| 6,027,741 A | 2/2000 | Cialdim et al. | |
| 6,042,262 A | 3/2000 | Hajianpour | |
| 6,045,570 A | 4/2000 | Epstein et al. | |
| 6,063,061 A | 5/2000 | Wallace et al. | |
| 6,066,325 A | 5/2000 | Wallace et al. | |
| 6,074,663 A | 6/2000 | Delmottet et al. | |
| 6,096,309 A | 8/2000 | Prior et al. | |
| 6,099,952 A | 8/2000 | Cercone | |
| 6,162,241 A | 12/2000 | Coury et al. | |
| 6,168,788 B1 | 1/2001 | Wortham | |
| 6,218,176 B1 | 4/2001 | Berthold et al. | |
| 6,261,596 B1 | 7/2001 | Li et al. | |
| 6,280,727 B1 | 8/2001 | Prior et al. | |
| 6,283,933 B1 | 9/2001 | D'Alessio et al. | |
| 6,300,128 B1 | 10/2001 | Morota et al. | |
| 6,303,323 B1 | 10/2001 | Laskey et al. | |
| 6,312,725 B1 | 11/2001 | Wallace et al. | |
| 6,334,865 B1 | 1/2002 | Redmond et al. | |
| 6,364,519 B1 | 4/2002 | Hughes et al. | |
| 6,387,413 B1 | 5/2002 | Miyata et al. | |
| 6,454,787 B1 | 9/2002 | Maddalo et al. | |
| 6,458,380 B1 | 10/2002 | Leaderman | |
| 6,461,325 B1 | 10/2002 | Delmotte et al. | |
| 6,495,127 B1 | 12/2002 | Wallace et al. | |
| 6,548,081 B2 | 4/2003 | Sadozai et al. | |
| 6,620,436 B1 | 9/2003 | Rolf | |
| 6,635,272 B2 | 10/2003 | Leaderman | |
| 6,638,538 B1 | 10/2003 | Hashimoto et al. | |
| 6,649,162 B1 | 11/2003 | Biering et al. | |
| 6,706,690 B2 | 3/2004 | Reich et al. | |
| 6,716,435 B1 | 4/2004 | Farmer et al. | |
| 6,733,774 B2 | 5/2004 | Stimmeder | |
| 7,052,713 B2 | 5/2006 | Stimmeder | |
| 7,125,860 B1 | 10/2006 | Renier et al. | |
| 7,427,607 B2 | 9/2008 | Suzuki | |
| 7,435,425 B2 | 10/2008 | Qian et al. | |
| 7,923,431 B2 * | 4/2011 | Wolff ..................... 514/13.7 | |
| 2001/0008636 A1 | 7/2001 | Yamamoto et al. | |
| 2001/0038848 A1 | 11/2001 | Donda | |
| 2001/0041913 A1 | 11/2001 | Cragg et al. | |
| 2002/0006429 A1 | 1/2002 | Redmond et al. | |
| 2002/0010150 A1 | 1/2002 | Cortese et al. | |
| 2002/0010482 A1 | 1/2002 | Watt et al. | |
| 2002/0012982 A1 | 1/2002 | Blakesley et al. | |
| 2002/0015724 A1 | 2/2002 | Yang et al. | |
| 2002/0019062 A1 | 2/2002 | Lea et al. | |
| 2002/0025921 A1 | 2/2002 | Petito et al. | |
| 2002/0026215 A1 | 2/2002 | Redmond et al. | |
| 2002/0039594 A1 | 4/2002 | Unger | |
| 2002/0042378 A1 | 4/2002 | Reich et al. | |
| 2002/0061842 A1 | 5/2002 | Mansour et al. | |
| 2002/0072767 A1 | 6/2002 | Zhu | |
| 2002/0111576 A1 | 8/2002 | Greene et al. | |
| 2002/0164322 A1 | 11/2002 | Schaufler | |
| 2002/0173818 A1 | 11/2002 | Reever | |
| 2002/0188196 A1 | 12/2002 | Burbank et al. | |
| 2002/0192271 A1 | 12/2002 | Hedner et al. | |
| 2002/0193448 A1 | 12/2002 | Wallace et al. | |
| 2003/0004449 A1 | 1/2003 | Lafratta et al. | |
| 2003/0008831 A1 | 1/2003 | Yang et al. | |
| 2003/0009194 A1 | 1/2003 | Saker et al. | |
| 2003/0012741 A1 | 1/2003 | Furlan et al. | |
| 2003/0028140 A1 | 2/2003 | Greff | |
| 2003/0032143 A1 | 2/2003 | Neff et al. | |
| 2003/0064109 A1 | 4/2003 | Qian et al. | |
| 2003/0095993 A1 | 5/2003 | Benz et al. | |
| 2003/0162708 A1 | 8/2003 | Wolff | |
| 2003/0181659 A1 | 9/2003 | Naranda et al. | |
| 2003/0232746 A1 | 12/2003 | Lamberti et al. | |
| 2004/0076647 A1 | 4/2004 | Biering | |
| 2004/0079763 A1 | 4/2004 | Powell et al. | |
| 2004/0101546 A1 | 5/2004 | Gorman et al. | |
| 2004/0120993 A1 | 6/2004 | Zhang et al. | |
| 2004/0197388 A1 | 10/2004 | Sceusa | |
| 2004/0214770 A1 | 10/2004 | Reich et al. | |
| 2004/0243043 A1 | 12/2004 | McCarthy et al. | |
| 2005/0008632 A1 | 1/2005 | Stimmeder | |
| 2005/0031691 A1 | 2/2005 | McGurk et al. | |
| 2005/0137512 A1 | 6/2005 | Campbell et al. | |
| 2005/0171001 A1 | 8/2005 | Pendharkar et al. | |
| 2005/0214277 A1 | 9/2005 | Schaufler | |
| 2005/0218541 A1 | 10/2005 | Peng et al. | |
| 2005/0245905 A1 | 11/2005 | Schmidt et al. | |
| 2006/0002890 A1 | 1/2006 | Hersel et al. | |
| 2006/0068013 A1 | 3/2006 | DiTizio et al. | |
| 2006/0159733 A1 | 7/2006 | Pendharkar et al. | |
| 2006/0189516 A1 | 8/2006 | Yang et al. | |
| 2006/0193846 A1 | 8/2006 | Stimmeder | |
| 2007/0009578 A1 | 1/2007 | Moller et al. | |
| 2007/0025955 A1 | 2/2007 | Lowinger et al. | |
| 2007/0264301 A1 | 11/2007 | Cleek et al. | |
| 2007/0264302 A1 | 11/2007 | Cleek et al. | |
| 2008/0095830 A1 | 4/2008 | Van Holten | |
| 2008/0311172 A1 | 12/2008 | Schapira et al. | |
| 2009/0087569 A1 | 4/2009 | Fan et al. | |

FOREIGN PATENT DOCUMENTS

| | | |
|---|---|---|
| BG | 0099900 | 3/1997 |
| DE | 3146841 | 6/1983 |
| DE | 4119140 | 12/1992 |
| DE | 4407875 | 9/1995 |
| EP | 0156649 | 10/1985 |
| EP | 0365705 | 5/1990 |
| EP | 0372966 | 6/1990 |
| EP | 0395758 | 11/1990 |
| EP | 0478827 | 4/1992 |
| EP | 0341745 | 12/1994 |
| EP | 0702081 | 3/1996 |
| EP | 0737467 | 10/1996 |
| EP | 0773740 | 11/1999 |
| EP | 1005874 | 6/2000 |
| EP | 1022031 | 7/2000 |
| EP | 1044693 | 10/2000 |
| EP | 1053758 | 11/2000 |
| EP | 1095064 | 5/2001 |
| EP | 1140235 | 10/2001 |
| EP | 1174463 | 1/2002 |
| EP | 1258256 | 11/2002 |
| EP | 0790823 | 7/2003 |
| EP | 0891193 | 8/2003 |
| EP | 1059957 | 8/2007 |
| FR | 2679772 | 2/1993 |
| FR | 2759980 | 8/1998 |
| GB | 648619 | 1/1951 |
| GB | 697603 | 9/1953 |
| GB | 1584080 | 2/1981 |
| GB | 2266239 | 10/1993 |
| GB | 2393120 | 3/2004 |
| GB | 2414021 | 11/2005 |
| JP | 60214728 | 10/1985 |
| JP | 62070318 | 3/1987 |
| JP | 62-221357 | 9/1987 |
| JP | 1-130519 | 5/1989 |
| JP | 06254148 | 9/1994 |
| JP | 10-507666 | 7/1998 |

| | | |
|---|---|---|
| JP | 2002-513308 | 5/2002 |
| JP | 2004-002271 | 1/2004 |
| WO | WO 89/02730 | 4/1989 |
| WO | WO 90/13320 | 11/1990 |
| WO | WO 93/06802 | 4/1993 |
| WO | WO 9306855 | 4/1993 |
| WO | WO 9310768 | 6/1993 |
| WO | WO 9321908 | 11/1993 |
| WO | WO 94/08552 | 4/1994 |
| WO | WO 94/17840 | 8/1994 |
| WO | WO 9512371 | 5/1995 |
| WO | WO 9525748 | 9/1995 |
| WO | WO 95/31955 | 11/1995 |
| WO | WO 96/07472 | 3/1996 |
| WO | WO 9616643 | 6/1996 |
| WO | WO 9640033 | 12/1996 |
| WO | WO 9717023 | 5/1997 |
| WO | WO 9717024 | 5/1997 |
| WO | WO 9717025 | 5/1997 |
| WO | WO 9729792 | 8/1997 |
| WO | WO 9737694 | 10/1997 |
| WO | WO 9808550 | 3/1998 |
| WO | WO 9831403 | 7/1998 |
| WO | WO 9836784 | 8/1998 |
| WO | WO 98/43092 | 10/1998 |
| WO | WO 9844963 | 10/1998 |
| WO | WO 9851282 | 11/1998 |
| WO | WO 9904828 | 2/1999 |
| WO | WO 99/12032 | 3/1999 |
| WO | WO 9938606 | 8/1999 |
| WO | WO 99/44901 | 9/1999 |
| WO | WO 9945938 | 9/1999 |
| WO | WO 0009018 | 2/2000 |
| WO | WO 00/18301 | 4/2000 |
| WO | WO 0027327 | 5/2000 |
| WO | WO 0061201 | 10/2000 |
| WO | WO 0074742 | 12/2000 |
| WO | WO 0076533 | 12/2000 |
| WO | WO 0113956 | 3/2001 |
| WO | WO 01/28603 | 4/2001 |
| WO | WO 01/34206 | 5/2001 |
| WO | WO 0154735 | 8/2001 |
| WO | WO 0166161 | 9/2001 |
| WO | WO 0197826 | 12/2001 |
| WO | WO 02/18450 | 3/2002 |
| WO | WO 0222059 | 3/2002 |
| WO | WO 0240068 | 5/2002 |
| WO | WO 02058749 | 8/2002 |
| WO | WO 03/007845 | 1/2003 |
| WO | WO 03/055531 | 7/2003 |
| WO | WO 03/070110 | 8/2003 |
| WO | WO 03094983 | 11/2003 |
| WO | WO 2004/028583 | 4/2004 |
| WO | WO 2004/035629 | 4/2004 |
| WO | WO 2004028404 | 4/2004 |
| WO | WO 2004028423 | 4/2004 |
| WO | WO 2004029095 | 4/2004 |
| WO | WO 2004030711 | 4/2004 |
| WO | WO 2004/053051 | 6/2004 |
| WO | WO 2004108035 | 12/2004 |
| WO | WO 2005000265 | 1/2005 |
| WO | WO 2005009225 | 2/2005 |
| WO | WO 2005/044285 | 5/2005 |
| WO | WO 2005041811 | 5/2005 |
| WO | WO 2005044285 | 5/2005 |
| WO | WO 2005062889 | 7/2005 |
| WO | WO 2006034568 | 4/2006 |
| WO | WO 2006063758 | 6/2006 |
| WO | WO 2007133699 | 11/2007 |
| WO | WO 2008051758 | 5/2008 |
| WO | WO 2008090555 | 7/2008 |
| WO | WO 2009109963 | 9/2009 |

OTHER PUBLICATIONS

Drognitz et al.; "Release of vancomycin and teicoplanin from a plasticized and resorbable gelatin sponge: in vitro investigation of a new antibiotic delivery system with glycopeptides."; Indection Germany (Minich); 34 (1); 2006; pp. 29-34.

Ellegala et al., Use of FloSeal Hemostatic Sealant in Transsphenoidal Pituitary Surgery, Technical Note, Aug. 2002, vol. 51, pp. 513-516, Neurosurgery.

English Derwent abstract of Ranjane reference, Nov. 18, 1997.

FloSeal Matrix Hemostatic Sealant. Instructions for Use, Retrieved on Aug. 17, 2005 from Internet Site http://www.ctsnet.org/file/vendors/931/pdf/140.pdf.

Gelfoam absorbable power, Accessed online at http://www.fda.gov/cdrh/pdf/N18286S012c.pdf on May 22, 2009.

Gelfoam RIM product information sheet, Jul. 2007.

Google search result showing disclosure of handled Gelfoam swab in the body of the Kelly publication, accessed online on May 11, 2009.

Google search, "Handled gelfoam swab", downloaded from <<http://www.google.com>>, accessed online on May 11, 2009.

Hae-Won et al.; "Porus scaffolds of gelatin-hydroxyapatite nanocomposites obtained by biometic approach: Characterization and antibiotic drug release."; J. of Biomedical Materials Research 74B(2); 2005; pp. 686-698.

Hill et al., Use of Microfibrillar Collagen Hemostat (Avitene) and Thrombin to Achieve Hemostasis After Median Sternotomy, 1994, vol. 108, pp. 1151-1152, J. Throac Cardiovasc. Surg.

Hill-West, et al., "Efficacy of a resorbable hydrogel barrier, oxidized regenerated cellulose and hyaluronic acid in the prevention of ovarian adhesions in a rabbit model", Fertility and Sterility 62(3):630-634 (1994).

Hong et al.; "Study on gelatin-containing artificial skin IV: a comparative study on the effect of antibiotic and EGF on cell proliferation during epidermal healing."; Biomaterials 22(20); 2001; pp. 2777-2783.

International Preliminary Examination Report for International Application No. PCT/DK03/00855 dated Jun. 6, 2005.

Kelly M. J. et al., "The value of an operative wound swab sent in transport medium in the prediction of later clinical wound infection: A controlled clinical and bacteriological evaluation", Brit. J. Surgery (1978), 65:2, pp. 81-88.

Kocak, et al., "Reduction of adhesion formation with cross-linked hyaluronic acid after peritoneal surgery in rats", Fertility and Sterility 72(5):873-878 (1999).

Larsson, et al., "Surgicel® —An absorbable hemostatic material—in prevention of peritoneal adhesion in rats", Acta Chir Scand. 144:375-378 (1978).

Laurent, et al., Hyaluronic acid reduces connective tissue formation in middle ears filled with absorbable gelatin sponge: An experimental study, AM. J. Otolaryngol 7:181-186 (1986).

Li, et al., "Evaluation of esterified hyaluronic acid as middle ear-packing material", Arch Otolaryngol Head Neck Surg 127:534-539 (2001).

Luengo, et al., "Prevention of peritoneal adhesions by the combined use of Spongostan and 32% Dextran 70: an experimental study in pigs", Fertility and Sterility 29(4) (1978).

M.G. Cascone et al.; "Collagen and hyaluronic acid based polymeric blends as drug delivery systems for the release of physiological concentrations of growth hormone." Journal of Materials science: Materials in Medicine; No. 5, 1994; pp. 770-774.

Maxson, et al., "Efficacy of a modified oxidized cellulose fabric in the prevention of adhesion formation", Gynecol. Obstet. Invest. 26:160-165 (1988).

Min et al. "Molecular Weight Changes of Sodium Hyaluronate Powder and Solution by Heat treatment," Matrix Biology Institute, Proceedings of Hyaluronan, Oct. 11-16, 2003.

Oz et al., Controlled Clinical Trial of a Novel Hemostatic Agent in Cardia Surgery, 2000, vol. 69, pp. 1376-1382,, Ann. Thorac. Surg.

Quintavalla, et al., "Fluorescently labeled mesenchymal stem cells (MSCs) maintain mutlilineage potential and can be detected following implantation into articular cartilage defects", Biomaterials 23:109-119 (2002).

Product leaflet for FloSeal® Matrix Hemostatic Sealant dated Jul. 2001.

Purdy et al., "Microfibrillar collagen model of canine cerebral infarction," Stroks, vol. 20 No. 10, Oct. 1989, p. 1361-1367.

Reijnen, et al., "Prevention of intra-abdominal abscesses and adhesions using a hyaluronic acid solution in a rat peritonitis model", Arch Surg. 134:997-1001 (1999).

Sakurabayashi et al.; "Clinical evaluation of new hemostatic agent for hemostasis from biopsy wounds in the liver."; Gastroenterological Endoscopy 30 (10); Oct. 1988.

Sanfilippo et al., Comparison of avitene, topical thrombin and Gelfoam as sole hemostatic agent in tuboplasties, Fertility and sterility 33(3):311-316 (1980).

Santomaso et al., "Powder flowability and density ratios: the impact of granules packing," Chemical Engineering Science 58 (2003) 2857-2874.

Shushan et al., "Hyaluronic acid for preventing experimental post-operative intraperitoneal adhesions", Journal of Reproductive Medicine 39(5):398-402 (1994).

Solar Biologicals Inc., "Solar-cult® sampling products: Pre-moistened cellulose sponge sampling systems", available atwww-w:solarbiologicals.com/samp-sys.htm (Jul. 25, 2002).

Soules et al., The prevention of postoperative pelvic adhesions: An animal study comparing barrier methods with Dextran 70", Am. J. Obstet. Gynecol. 143(7):829-834 (1982).

Spence et al., "Cerebellar capillary hemangioblastoma: Its histogenesis studied by organ culture and electron microscopy", Cancer 35(2):326-341 (1975).

Stuart Transport medium information sheet, accessed online on May 27, 2009.

Stuart Transport Medium, Catalog item 1518, p. 215, downloaded from <<http://www.condalab.com>>, accessed online on May 27, 2009.

Swann, "Studies on hyaluronic acid—I. The preparation and properties of rooster comb hyaluronic acid," Biochemica et biophysica acta, 156 (1968) p. 17-30.

Van Der Salm T.J. et al.; "Reduction of sternal infection by application of topical vancomycin."; J. of Thoracic and Cardiovascular Surgery; vol. 98, No. 4; 1989; pp. 618-622.

Wachol-Drewek et al.; "Comparative investigation of drug delivery of collagen implants saturated in antibiotic solutions and a sponge containing gentamicin."; Biomaterials 17; 1996; pp. 1733-1738.

West et al., "Efficacy of adhesion barriers: Resorbable hydrogel, oxidized regenerated cellulose and hyaluronic acid", The Journal of Reproductive Medicine 41((3):149-154 (1996).

Wiesenthal et al.; "New method for packing the external auditory canal, middle ear space, and mastoid cavities after otologic surgery."; The Journal of Otolaryngology; vol. 28, No. 5; 1999; pp. 260-265.

Y.S. Choi et al., "Studies on gelatin-containing artificial skin: II. Preparation and characterization of cross-linked gelatin-hyaluronate sponge" J Biomed Mater Res 1999; 48. pp. 631-639.

Yuesong et al.; "Design and experimental study of a slow-release antibiotic membrane implant in surgery wound."; Intern. Des Services de San. Des Forces Armees; vol. 72, No. 7-9; Sep. 1999; pp. 194-196.

Cantor et al., "Gelfoam® and Thrombin in Treatment of Massive Gastroduodenal Hemorrhage," American Journal of Surgery, pp. 883-887 Dec. 1950.

Harris et al., "Topical Hemostatic Agents for Bone Bleeding in Humans," J. of Bone and Joint Surgery, pp. 454-456, 1978.

Schramm et al., "Gelfoam Paste Injection for Vocal Cord Paralysis: Temporary Rehabilitation of Glottic Incompetence," The Laryngoscope, 88, pp. 1268-1273, 1978.

Taheri, "The Use of Gelfoam Paste in Anterior Cervical Fusion," J. Neurosurg., 34, p. 438, Mar. 1971.

Wilkinson et al., "Gelfoam Paste in Experimental Laminectomy and Cranial Trephination," J. Neurosurg, 54, pp. 664-667, 1981.

* cited by examiner

HAEMOSTATIC KIT, A METHOD OF PREPARING A HAEMOSTATIC AGENT AND A METHOD OF PROMOTING HAEMOSTASIS

This application is a continuation under 35 U.S.0 §120 of U.S. patent application Ser. No. 10/326,080, filed Dec. 23, 2002, which claims benefit of priority to U.S. Provisional Application Ser. No. 60/367,515, filed Mar. 27, 2002 and U.S. Provisional Application Ser. No. 60/341,812, filed Dec. 21, 2001, the contents of which are hereby incorporated by reference in their entirety.

FIELD OF THE INVENTION

A medical device comprising a powdered haemostatic agent in a containment unit suitable for adding a liquid to the agent and mixing the contents whilst still in the container allows for the sterile use of the haemostatic agent and greater ease of preparation. The haemostatic agent, such as collagen or a collagen-derived product such as gelatin, is present in a 1-volume in the containment unit to allow for suitable mixing of any further agents, such as water, saline, or thrombin.

BACKGROUND OF THE INVENTION

The use of haemostatic agents provides for control of bleeding in surgical procedures. Haemostatic agents supplement pressure, ligature and other conventional methods of controlling capillary, venous, and arterial bleeding.

The present investigators have commercialised a gelatin sponge as a haemostatic agent. A powdered agent some practical advantages in terms of surface area coverage and can be removed by irrigation and suction. Conventional powdered haemostatic agents are unpractical and risk either contamination of the sterile surgical field. The present invention addresses the risk of compromised sterility and contamination of the haemostatic agent by providing a kit which allows for the sterile and facile preparation of the powdered haemostatic agent.

WO 01/28603 relates to an injectable formulation for delivery of a composition comprising an osteogenic protein and a haemostatic gelatin foam paste as well as to a method of making a haemostatic gelatin foam paste suitable for injecting osteogenic protein, the method comprising hydration of Gelfoam® powder with glutamic acid buffer.

U.S. Pat. No. 5,394,886 relates to a skin biopsy plug wherein the plug is a porous sponge made from gelatin material, which is implanted into a wound, swells, absorbs blood, and is completely absorbed in the patient. It relates to a combination of the punch (the blade for excising skin) and the plug. The plug used is the commercially available Gelfoam®.

U.S. Pat. No. 5,645,849 claims a haemostatic patch comprising a biodegradable gelatin matrix, a haemostatic-promoting amount of thrombin and epsilon aminocaproic acid.

JP 62221357 discloses a skin ointment for promoting haemostatic effect comprising thermoplastic resin or rubber dissolved in solvent and contains dispersed gelatin powder. The product is an ointment comprising thermoplastic resin or rubber and a fine powder of collagen, gelatin or chitosan.

FR 2679772 relates to particulate material to create an embolism comprising a polymer coated with a haemostatic or thrombonic agent. The haemostatic agent may be a finely divided gelatin powder.

U.S. Pat. No. 6,096,309 relates to a haemostatic composition comprising thrombin and a mixture of non-microfibrillar collagen and microfibrillar collagen in an aqueous medium wherein the microfibrillar collagen has an average fibril diameter of about 3-30 nm.

U.S. Pat. No. 4,515,637 relates to both a method of forming a collagen-thrombin haemostatic composition and to a lysophilized collagen product, comprising collagen and thrombin.

U.S. Pat. No. 6,045,570 relates to a gelatin powder for use as a haemostatic agent and to a biological sealant comprising a gelatin slurry which includes milled gelatin powder. The slurry preferably comprises Gelfoam® powder mixed with a diluent selected from saline and water. The slurry demonstrates superior flow characteristics in that it exhibits minimal dilatency and can be easily injected or introduced through catheter lumens, especially small lumens. The product therefore has very fluid characteristics.

Gelfoam® is a commercially available product providing powdered gelatin for application to bleeding surfaces as a haemostatic agent. The powdered gelatin is provided in a full glass jar with a metal lid or in a sachet, each of which are to be opened and the contents of which, i.e. the gelatin, are to be poured into a sterile beaker or bowl. Contamination must be avoided during this process and a sterile technique must be employed when adding a sterile saline solution. The problem of dispersion is avoided by initially compressing the powder with gloved fingers into the bottom of the beaker and then kneading it into the desired consistency. The powder is to be used as soon as the jar or sachet is opened and unused portions are discarded. This requires preparation of the haemostatic agent immediately prior to use. Contamination and sterility is not controlled by the product but rather by the user and by the co-ordination of events following preparation of the agent.

Curacell® is a powdered haemostatic agent comprising oxidised cellulose, caboxycellulosum calcium which is applied as dry powder onto a bleeding area.

Avitene® is a microfibullar collagen haemostat "flour" typically applied dry.

SUMMARY OF THE INVENTION

A first object of the invention relates to a medical device comprising:
  i) a containment unit defining a first internal volume; said containment unit being comprised of a material substantially impermeable to fluid;
  ii) a haemostatic agent of a second volume contained in said containment unit, said second volume being less than 90% of the first volume.

A further object of the invention relates to a haemostatic kit comprising
  i) a containment unit said containment unit defining a first internal volume and
  ii) a second volume of haemostatic agent
  wherein the second volume relative to the first internal volume is such that the kit is suitable adding a third volume of liquid to said second volume and suitable for mixing said haemostatic agent within said containment unit.

Moreover, the invention relates to a process for preparing a haemostatic product comprising the steps of:
  i) providing a sterile containment unit having a first internal volume and at least one aperture for opening and comprising a second volume of haemostatic agent, said second volume being no more than 90% of the first volume;
  ii) adding a third volume of liquid to said containment unit; and
  iii) mixing the haemostatic agent and the liquid by shaking the containment unit.

A corresponding aspect of the invention relates to a method of promoting haemostatis comprising administering an effective amount of a putty-like paste comprising 20 to 33% w/w of collagen to a patient in need of haemostatis, wherein the putty-like paste is prepared according process defined supra.

An important object of the invention relates to the use of a containment unit defining a first internal volume and second volume of collagen or collagen-derived powder for the preparation of a haemostatic kit wherein the second volume is less than 90% of the first volume.

An important object of the invention relates to the use of a containment unit defining a first internal volume and second volume of collagen or collagen-derived powder for the preparation of a haemostatic kit wherein the second volume is less than 90% of the first volume.

DESCRIPTION OF THE INVENTION

Figure 1:
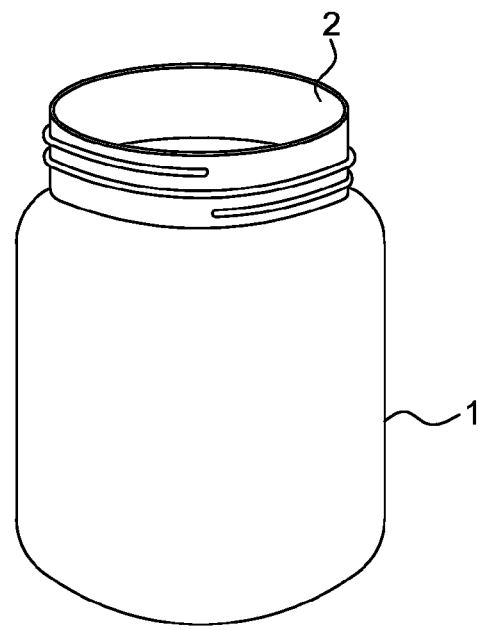
FIG. 1 is a schematic illustration of a containment unit (1) comprising an opening to an external environment (2).
Figure 2:
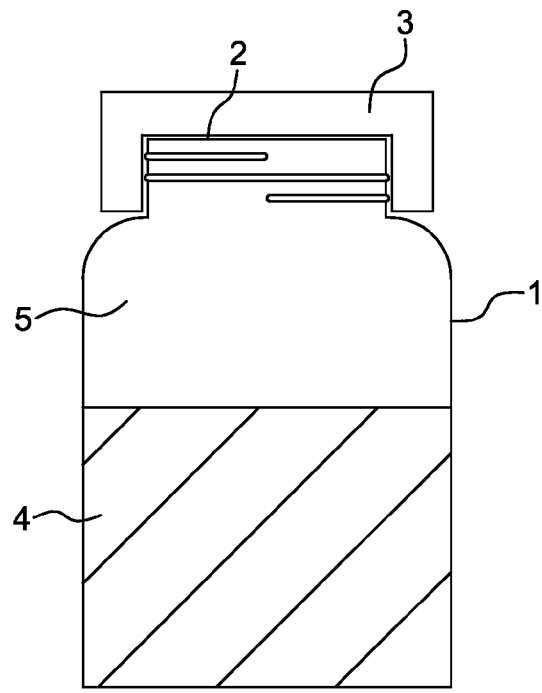
FIG. 2 is a schematic illustration of a containment unit (1), where the opening (2) is closed with a closure-unit (3). Within the containment unit is a haemostatic agent in powder form (4) and a void volume (5).
Figure 3:
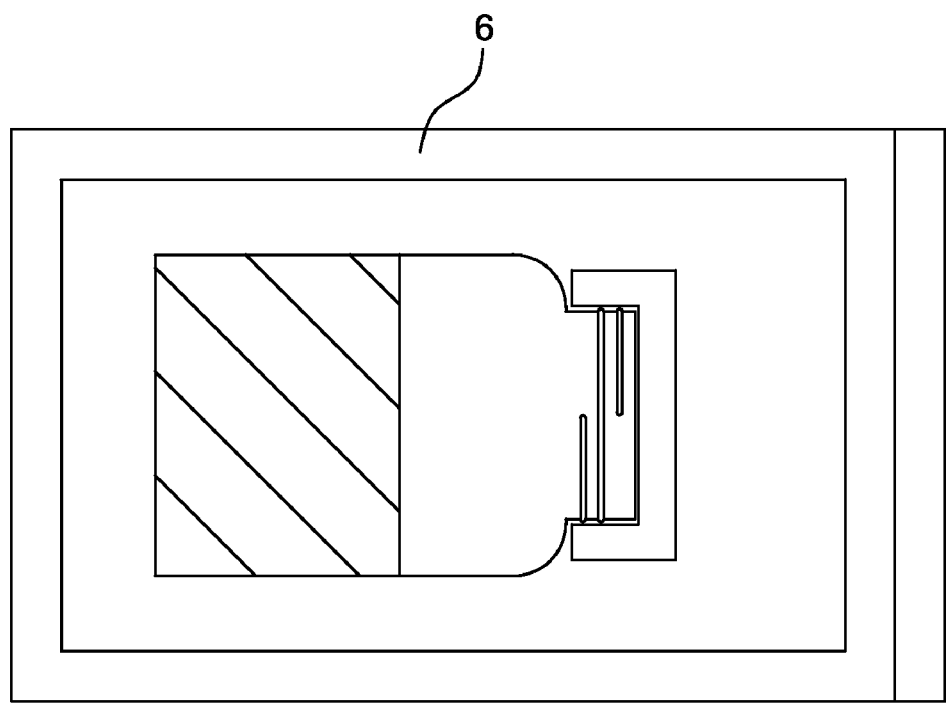
FIG. 3 is a schematic illustration showing an outer packaging (6) enclosing the containment unit.

The risk of compromised sterility and contamination of the haemostatic agent is addressed by the present investigators by providing a kit and medical device which allows for the sterile and facile preparation of the powdered haemostatic agent. The present invention also allows for greater flexibility and ease of preparation of the agent. Surgeons state that the size of the bleeding area and the rate of the bleeding generally determine the consistency and amount of haemostatic agent. During a surgical procedure, these factors can suddenly and dramatically change. The present invention allows for a rapid, sterile and facile preparation of the haemostatic agent. As stated, conventional products typically require the surgical staff to prepare the agent in advance using an additional mixing container.

A first aspect of the invention relates to a medical device comprising:

i) a containment unit defining a first internal volume; said containment unit being comprised of a material substantially impermeable to fluid; and ii) a haemostatic agent of a second volume contained in said containment unit, said second volume being less than 90% of the first volume.

The term "second volume" is intended to mean a volume which is a subset within the first internal volume. That is to say that the second volume of the haemostatic agent is contained within the first internal volume; that the agent is contained within the containment unit.

The medical device is preferably such that the second volume is less than 85%, of the first volume, preferably less than 80%, even more preferably less than 75% of the first volume, such as less than 70%, 65%, 60%, 55%, or 50% of the first volume, such as 70%, 65%, 60%, 55%, 50%, 40%, 30%, 20% and 10%.

In a typical embodiment, the haemostatic agent is in powder form. In a more typical embodiment, the haemostatic agent is collagen or collagen-derived powder. Preferably, said collagen or collagen-derived powder is gelatin. The gelatin may be derived from an animal or are synthetically made (recombinant). Suitably, the gelatin originates from porcine but may originate from other mammals. The powder is typically sterile.

The powder is typically such that 95% of the powder is less than 1000 microns in size, preferably such that 90% of the second volume is less than approximately 700 μm. In a further preferred embodiment, 50% volume is less than approximately 350 μm.

The powder may be prepared from a gelatin sponge cut into pieces that fit into a mill and that will be bulk packaged into sterilization bags and placed in an oven (dry heat), for hardening for three hours. The gelatin plates raw material are typically manually fed into a rotor knife mill with a sieve for final grinding. The particle size is preferably such that not more than 5% (w/w) is retained on a 1 mm mesh.

The containment unit typically comprises at least one opening and at least one closure-unit for closing the at least one opening. In an interesting embodiment, the closure-unit defines a second internal volume suitable for containing a liquid. The liquid may be present in the closure-unit and this liquid can be released into the gelatin by a mechanical or physical action.

The closure-unit may itself comprise a rupturable membrane or the containment unit may comprise a rupturable membrane. This membrane may define a physical separation between the second internal volume and the internal volume defined by the first internal volume and may allow for the combining of the liquid with the haemostatic agent by means of rupturing the membrane by any physical act such as by pressure or contact. The membrane may be ruptured (broken) by means of shaking the device. The rupturing of the membrane is preferably performed in such a manner so as to maintain the sterility of the liquid and of the haemostatic agent.

Alternatively, the closure unit or containment unit may comprise a rupturable membrane which is perforated in order to inject the liquid, such as to maintain sterility of the agent. In this embodiment, the rupturable membrane divides the external environment from the first and/or second internal volume. The rupturable membrane may be made of rubber or other suitable material and be perforated by injection of the liquid through a syringe or catheter.

The containment unit may comprise of grooves, protrusions or other physical distortions to the otherwise parallel surfaces of the juxtaposed walls of the containment unit so as to ameliorate or facilitate the mixing of a liquid and the haemostatic agent.

In the embodiment wherein the haemostatic agent is collagen or collagen-derived powder, such as gelatin, it is suitably present in an amount from about 0.1 to 50 g, preferably from about 0.2 to 20 g, even more preferably from about 0.4 to 10 g, most preferably from about 0.5 to 5 g, such as 0.75, 1, 1.5, 2, 2.5, 3, 3.5, 4, 4.5, and 5 g.

The containment unit is typically substantially rigid with at least one opening which may be closed with an appropriate closure-unit. The containment unit and closure unit are typically comprised of a material independently selected from the group consisting of plastic, glass, metal or rigid or semi-rigid material. In a preferred embodiment, the material is selected from the group consisting of polypropylene, polyethylene, PVC and PET, more preferably polypropylene and polyethylene, most preferably polyethylene. Polyethylene is most suitable for beta irradiation. The substantially rigid polyethylene or polypropylene container having a single opening may be sealed with a threaded, polyethylene or polypropylene closure. The closure-unit suitably comprises a dust-seal closure.

As stated, the containment unit defines a first internal volume; internal volume comprising a haemostatic agent of a second volume, said second volume being less than 90% of the first volume. The volume difference is, at least in part, to allow for adequate addition of a third volume and mixing of the volumes. The dimension of the containment unit is suitably to facilitate the mixing. Typically, the dimension of the containment unit is also selected so as to allow for facile removal of the volumes onto the patient or other desired location. Thus, the mouth of the containment unit must be suitably broad. Thus, commercially available wide-mouth or large-mouth containers are preferred.

In a particularly suitable embodiment, the haemostatic agent is present in a volume occupied by about one gram of powder, said second volume of haemostatic agent is contained within a containment unit of about 50 to 100 cubic centimetres, such as about 60 to 90 cubic centimetres, such as about 70 to 80 cubic centimetres, typically about 75 cubic centimetres.

In the suitable embodiment wherein the haemostatic agent is present in a volume occupied by about two grams of powder, said second volume of haemostatic agent is contained within a containment unit of about 75 to 200 cubic centimetres, such as about 80 to 180 cubic centimetres, such as about 90 to 170 cubic centimetres, such as about 100 to 160 cubic centimetres. Typically a second volume occupied by 2 g of powder is contained within a first internal volume of 100 to 200 cubic centimetres.

The medical device suitably further comprises iii) a third volume of a liquid. The liquid may blended with the haemostatic agent.

In a suitable embodiment, the liquid is in a unit physically separated from the haemostatic agent. This physical separation may be in the form of a rigid internalised container in the containment unit or merely by means of a physical barrier which creates a non-porous divide between the agent and the liquid.

In an alternative embodiment, the liquid is in a second containment unit whose internal volume is physically separated from the first containment unit, such as to form a kit.

In a suitable embodiment, the liquid is thrombin. Thus, the medical may further comprise thrombin. The thrombin may be present in the first containment unit or may be in a unit physically separated from the haemostatic agent or in a second containment unit containing said thrombin.

Thrombin, in a particularly suitable embodiment, may be added in an amount of 1-20 ml per gram of powder, such as 5-15 ml, such as 7-12 ml.

The liquid may alternatively be selected from the group consisting of water and an aqueous solution such as saline. Suitably, the aqueous solution comprises an isotonicity-adjusting agent. The isotonicity adjusting agent may be sodium chloride, or known equivalents to sodium chloride such as dextrose, various organic acids and their salts, inorganic salts such as boric acid, citric acid, tartaric acid and phosphoric acids.

The liquid may comprise thrombin and/or a bacteriostatic agent. Typically, the liquid is sterile.

In a typical embodiment, the third volume of liquid is less than 35% of the second volume. The volume of liquid is preferably such that, when combined and mixed with the haemostatic agent, a doughy paste is formed. More suitably, the third volume is less than 33% of the second volume, such as less than 30%, less than 29%, less than 28%, less than 27%, less than 26%, less than 25%, less than 24%, less than 23%, less than 22%, less than 21%, or less than 20%.

The mixing of the liquid and the haemostatic agent is preferably performed by shaking the containment unit, most preferably the mixing is performed when the at least one opening is separated from the external environment by the closure-unit. Shaking may involve swirling or agitation of any kind.

In a particularly interesting embodiment, the containment unit is surrounded with on outer wrap so that the containment unit is sterile. This will allow the user to remove the outer packaging and transfer the containment unit into the sterile field. The user, in the sterile field, can then add the third volume of liquid, optionally by opening the containment unit to the external environment, adding by means of perforating the rupturable membrane of the closure-unit or containment unit, rupturing a seal which divides the closure unit from the containment unit, as discussed supra, or pouring the liquid through the at least one opening of the containment unit.

The medical device preferably further comprises an outer packaging defining a sterile barrier seal for enclosing said containment unit and maintaining sterility of the containment unit and its contents. The outer packaging may be peelable or removed from the outer surface of the containment unit. This containment unit is preferably enclosed in an outer packaging of a flexible, semi-rigid, or rigid plastic and/or metallic film providing a sterile barrier. The outer packaging typically consists of materials selected from the group consisting of Plastic/Aluminium foil/Plastic laminate where the plastic is selected from the group consisting of PET, PE, LLDPE, CPP, PA, PETP, METPET, Tyvek and optionally bonded with an adhesive (Polyurethane or other) or co-extruded. The outer packaging preferably forms a complete barrier to moisture.

The outer packaging may, in a particularly interesting embodiment, be able to endure radiation sterilisation at 3.5 Mrad (Beta) with a bioburden of less than 100 CFU/unit. A particularly interesting embodiment of the outer packaging included a pouch of laminated foil. The laminate may be PET, such as of approximately 12 microns in thickness.

The containment unit is preferably sterile. The containment-unit-facing side of the outer packaging and the containment unit are preferably sterile.

The liquid is typically added so as to obtain a paste-like agent comprising 20-35% wt/wt of w/w collagen powder, such as 25-33%, such as 25%, 26%, 27%, 28%, 29%, 30%, 31%, 32% and 33%.

A further object of the invention relates to a haemostatic kit comprising
 i) a containment unit said containment unit defining a first internal volume; and
 ii) a second volume of haemostatic agent
 wherein the second volume relative to the first internal volume is such that the kit is suitable to adding a third volume of liquid to said second volume and suitable for mixing said haemostatic agent said mixing proceeding within the containment unit.

Preferably, the mixing occurs without present exposure to an environment external to that of the containment unit, typically without exposure to a non-sterile field.

The relative volume of the second volume of haemostatic agent relative to the first internal volume is less than in conventional products so as to be suitable for adding a third volume of liquid and for said liquid to be evenly and easily physically dispersed throughout the second volume of haemostatic agent. Moreover, the mixing process, which accelerates the dispersion of the liquid evenly throughout the second volume of haemostatic agent, is facilitated and ameliorated by a low second volume-to-first volume ratio.

Thus, in a particularly preferred embodiment, the second volume of haemostatic agent is less than 85% of the first internal volume, such as less than 80% of the first volume, preferably less than 75%, even more preferably less than 70% of the first volume 65%, 60%, 55%, or 50% of the first volume.

The mixing process occurs within the containment unit and typically without present exposure to an environment external to that of the containment unit. That is to say that a physical barrier, such as a closure-unit, typically separates the first internal volume, second volume of haemostatic agent and third volume of liquid from the external environment during the mixing process.

The third volume is an amount so as to obtain a putty-like paste from the haemostatic agent, preferably wherein the putty-like paste of the haemostatic agent comprises 20-35% wt/wt of w/w collagen powder, such as 25-33%, such as 25%, 26%, 27%, 28%, 29%, 30%, 31%, 32% and 33%.

The containment unit is typically rigid, comprising at least one opening and one closure-unit and such that the mixing proceeds without loss of liquid and as described supra. The containment unit may be surrounded by a outer wrap/outer packaging se described supra.

A further aspect of the invention relates to a process for preparing a haemostatic product comprising the steps of:
i) providing a sterile containment unit having a first internal volume and at least one aperture for opening and comprising a second volume of haemostatic agent, said second volume being no more than 90% of the first volume;
ii) adding a third volume of liquid to said containment unit; and
iii) mixing the haemostatic agent and the liquid by shaking the containment unit.

Typically, the mixing proceeds without present substantial exposure of said haemostatic agent and said liquid to an environment external to that the containment unit and without exposure to a non-sterile field. Preferably, the haemostatic agent is collagen or collagen-derived powder, typically said collagen or collagen-derived powder comprises essentially of gelatin.

Preferably, in the process of the invention for preparing a haemostatic product, said haemostatic product is in the form of a putty-like paste comprising 20 to 99% w/w of collagen, preferably 20-80% collagen, such as 20-75% collagen, typically 20-70% collagen, such as 20-50%, 20-40%, 20-35%, 25-35%, such as 25%, 26%, 27%, 28%, 29%, 30%, 31%, 32%, 33%, 34%, and 35% w/w.

The process typically involves the containment unit being rigid, and comprising at least one opening and one closure-unit and such that the mixing proceeds without loss of liquid.

The second volume is typically less than 85% of the first volume, preferably less than 80%, even more preferably less than 75% of the first volume, such as 70%, 65%, 60%, 55%, or 50% of the first volume.

The process for preparing a haemostatic product may comprise the steps of:
i) providing a containment unit having a first internal volume and at least one aperture for opening said aperture closed by a closure-unit and comprising a second volume of 15 haemostatic agent, said second volume being no more than 90% of the first volume;
ii) adding a third volume of liquid to said containment unit; and
iii) mixing the haemostatic agent and the liquid by shaking the containment unit.

The sterile containment unit may further comprise an outer packaging defining a sterile barrier seal for enclosing said containment unit, as described supra.

A further aspect of the invention relates to a method of promoting haemostatis comprising administering an effective amount of a putty-like paste comprising 20-35% wt/wt collagen powder, such as 25-33%, such as 25%, 26%, 27%, 28%, 29%, 30%, 31%, 32% and 33% of collagen to a patient in need of haemostatis, wherein the putty-like paste is prepared according process as defined supra.

The invention may be for use in any array of surgical procedures wherein bleeding or fluid control is preferred, such as in orthopedic procedures, such as laminectomy, total hip replacement and hip revisions, knee surgery, spinal fusion; in cardiothoracic/cardiovascular procedures such as CABGs, valve replacements, aotic surgery, abdominal aortic aneurisms, carotid endarterectomy, and femoral-popliteal bypass, amongst others.

A still further object of the invention is directed to the use of a containment unit defining a first internal volume and a second volume of collagen or collagen-derived powder for the preparation of a haemostatic kit; wherein the second volume is less than 90% of the first volume such as 85% of the first internal volume, such as less than 80% of the first volume, preferably less than 75%, even more preferably less than 70% of the first volume 65%, 60%, 55%, or 50% of the first volume.

The invention is further defined by the Examples.

EXAMPLES

Example 1

Product and Preparation

Clinical data (Example 2) was obtained on powder prepared from milling sheets of Surgifoam® sponge under a controlled process to produce a product meeting the following specification:

The powder is a porcine gelatin based powder, off white in colour.

10% volume is less than approximately 90 µm;

50% volume is less than approximately 350 µm;

90% volume is less than approximately 700 µm;

as determined by laser diffraction.

The milled product is collected under slight negative pressure to avoid particulate emission in the area and filled into a primary container, such as by using a hopper and scoop filling operation or by using pharmaceutical cGMP standard auger filling equipment.

The fill will be such that to be less than 75% of the volume of the primary container and checked by electronic scales so as to meet to desired pre-determined weight. A closure will be applied.

The container will then be placed in a foil/film pouch which is sealed with a rotary heat sealer to form a moisture protection poach.

Alternatively, the batched containers will then be transferred to a blister packing room, such as a Multivac blister packing, where each container is packaged into a PETG/PE blister package. The blister packed product is loaded into irradiation boxes and subjected to pre-determined levels of e-beam irradiation.

Example 2

Clinical Data

Clinical tests for effectiveness on general surgical procedures as well as cardiovascular and orthopaedic surgical procedures were performed.

Study Design

An open label, randomised, controlled, multi-centre, unmasked study was conducted to evaluate safety and effectiveness of two haemostatic agents. The study compared the SURGIFOAM sponge from which the haemostatic powder is prepared to an absorbable gelatin sponge currently legally marketed in the USA. The primary objective was to examine the effectiveness as measured by haemostatis within 10 minutes of application.

Study Results

Two hundred and eighty one patients were enrolled in to the study and received study treatment. The haemostatis data was collected immediately during the surgery and the patients examined at 2 to 4 weeks and again at 6 to 8 weeks in order to obtain safety data. The effectiveness data is summarised in Table 1.

TABLE 1

| Minutes | Device | General % | Cadiovascular % | Orthopaedic % | Total % |
|---|---|---|---|---|---|
| 3 | Surgifoam | 65.6 | 57.4 | 91.7 | 64.0 |
|  | Control | 66.2 | 62.9 | 100 | 66.9 |
| 6 | Surgifoam | 98.4 | 80.9 | 100 | 90.1 |
|  | Control | 95.4 | 91.9 | 100 | 94.2 |
| 10 | Surgifoam | 100 | 89.7 | 100 | 95.1 |
|  | Control | 95.4 | 96.8 | 100 | 96.4 |

Statistical analysis showed that SURGIFOAM and the control sponge were equivalent in the ability to achieve haemostatis within 10 minutes.

Example 3

Evaluation of the Medical Device

Goal

The purpose of this study was to measure both surgeons and operating room nurses' perception of the device in terms of control of sterility and ease of preparation.

Method/Sample 12 interviews were conducted with operating room nurses who use haemostatic agents regularly.

Summary of Results

The surgeons and the nurses had complete acceptance and preference for a kit as defined by the present invention over conventional products.

Conventional Practice

Mixing of Conventional Products:
use of finger in a container separate than the agents container
use of forceps or pickups or other surgical instruments in a container separate than the agents container Disadvantages of Conventional Products:
possible contamination in transferring product to separate mixing container
bad smell
non-sterile packaging
powder is readily air-borne during opening and transfer process
non-sterile container risks contamination of sterile field
lengthy preparation due to requirement of additional bowl
breathing in of air-borne powder
wasted product in dispensing to mixing container A medical device of the present invention was presented to the surgeons and the nurses of the test study. The response was such that the invention favourably addressed most or all of the disadvantaged of conventional products.

Example 4

Sealed Pouches of Laminated Foil for Containment Unit

The pouch must be able to endure radiation sterilisation at 3.5 Mrad (Beta) Bioburden less than 100 CFU/unit. With the Pouch A, suitable containment comprising 1 gram of powder allowed for the storage of the powder and the containment unit as sterile for extended periods of time (typically at least 4 years) without loss in the quality of the materials.

| Material: | PET | 12 microns |
|---|---|---|
|  | Foil | 8.75 microns |
|  | Clear EZ Peel | 50 microns |
| Size: | Width | 6.5 inches |
|  | Length | 10 inches, | with a thumbnotch at the chevron end to allow for easy opening.

Provider Perfecseal

Items

1. A medical device comprising:
   i) a containment unit defining a first internal volume; said containment unit being comprised of a material substantially impermeable to fluid;
   ii) a haemostatic agent of a second volume contained in said containment unit, said second volume being less than 90% of the first volume.

2. The medical device according to item 1, wherein said second volume is less than 85%, of the first volume, preferably less than 80%, even more preferably less than 75% of the first volume, such as 70%, 65%, 60%, 55% or 50% of the first volume.

3. The medical device according to any one of items 1 to 2, wherein the haemostatic agent is collagen or collagen-derived powder.

4. The medical device according to item 3, wherein said collagen or collagen-derived powder is gelatin.

5. The medical device according to any one of the preceding items further comprising iii) a third volume of a liquid 6. The medical device according to item 5, wherein the liquid is blended with the haemostatic agent 7. The medical device according to item 5, wherein the liquid is in a unit physically separated from the haemostatic agent 8. The medical device according to item 5, wherein the liquid is in a second containment unit whose internal volume is physically separated from the first containment unit.

9. The medical device according to any one of preceding items further comprising thrombin or a containment unit containing thrombin.

10. The medical device according to item 5, wherein the liquid is selected from the group consisting of water and an aqueous solution.

11. The medical device according to item 10, wherein the aqueous solution comprises an isotonicity-adjusting agent.

12. The medical device according to item 11, wherein the isotonicity adjusting agent is sodium chloride.

13. The medical device according to any one of items 5 to 12, wherein the liquid comprises thrombin and/or a bacteriostatic agent.

14. The medical device according to items 4 to 13, wherein the liquid is sterile.

15. The medical device according to any one of preceding items, wherein said containment unit comprises at least one opening and at least one closure-unit for closing the at least one opening.

16. The medical device according to item 15, wherein the closure-unit comprises a rupturable membrane.

17. The medical device according to any one of items 15 to 16, wherein the closure-unit defines an internal volume suitable for containing a liquid.

18. The medical device according to items 4 to 12, wherein the third volume of liquid is less than 20% of the second volume.

19. The medical device according to any one of preceding items, wherein said collagen or collagen-derived powder is in an amount from about 0.1 to 50 g, preferably from about 0.2 to 20 g, even more preferably from about 0.4 to 10 g, most preferably from about 0.5 to 5 g, such as 0.75, 1, 1.5, 2, 2.5, 3, 3.5, 4, 4.5, and 5 g.

20. The medical device according to any one of preceding items further comprising an outer packaging defining a sterile barrier seal for enclosing said containment unit.

21. The medical device according to any one of preceding items, wherein the containment unit is sterile.

22. The medical device according to any one of items 20 to 21 wherein the containment unit-facing side of the outer packaging and the containment unit are sterile.

23. A haemostatic kit comprising
  i) a containment unit said containment unit defining a first internal volume and
  ii) a second volume of haemostatic agent
  wherein the second volume relative to the first internal volume is such that the kit is suitable adding a third volume of liquid to said second volume and suitable for mixing said haemostatic agent within said containment unit.

24. The haemostatic kit according to item 23, wherein the third volume is an amount so as to obtain a putty-like paste from the haemostatic agent, wherein a putty-like paste of the haemostatic agent comprises 20-33% w/w of collagen powder.

25. A method according to item 23, wherein said mixing proceeds without present exposure to an environment external to that of the containment unit.

26. The haemostatic kit according to any one of items 23 to 24, wherein the containment unit is rigid, comprises at least one opening and one closure-unit and such that the mixing proceeds without loss of liquid.

27. The haemostatic kit according to any one of items 23 to 26, wherein the second volume of haemostatic agent is less than 90% of the first internal volume.

28. The haemostatic kit according to item 27, wherein said second volume is less than 90% of the first volume, preferably less than 85%, even more preferably less than 80% of the first volume, such as 75%, 70%, 65%, 60%, 55% or 50% of the first volume.

29. The haemostatic kit according to any one of items 23 to 27, wherein the haemostatic agent is collagen or collagen-derived powder.

30. The haemostatic kit according to item 29, wherein said collagen or collagen-derived powder comprises essentially of gelatin.

31. The haemostatic kit according to item 26, wherein the closure-unit comprises a rupturable membrane.

32. The haemostatic kit according to any one of items 23 to 31 further comprising iii) said third volume of a liquid 33. The haemostatic kit according to item 32, wherein the liquid is blended with the haemostatic agent.

34. The haemostatic kit according to item 32, wherein the liquid is in a unit physically separated from the haemostatic agent.

35. The haemostatic kit according to item 32, wherein the liquid is in a second containment unit whose internal volume is physically separated from the first containment unit.

36. The haemostatic kit according to any one of items 23 to 35 further comprising thrombin or a containment unit containing thrombin.

37. The haemostatic kit according to item 32, wherein the liquid is selected from the group consisting of water and an aqueous solution.

38. The haemostatic kit according to item 37, wherein the aqueous solution comprises an isotonicity-adjusting agent.

39. The haemostatic kit according to item 38, wherein the isotonicity adjusting agent is sodium chloride.

40. The haemostatic kit according to any one of items 23 to 39, wherein the liquid comprises thrombin and/or a bacteriostatic agent.

41. The haemostatic kit according to items 23 to 40, wherein the liquid is sterile.

42. The haemostatic kit according to any one of preceding items, wherein said containment unit comprises at least one opening and at least one closure-unit for closing the at least one opening.

43. The haemostatic kit according to item 26, wherein the closure-unit defines an internal volume suitable for containing a liquid.

44. The haemostatic kit according to items any one of items 23 to 43, wherein liquid is an amount less than 20% of the second volume.

45. The haemostatic kit according to any one of items 23 to 44, wherein said haemostatic agent is in an amount from about 0.1 to 50 g, preferably from about 0.2 to 20 g, even more preferably from about 0.4 to 10 g, most preferably from about 0.5 to 5 g, such as 0.75, 1, 1.5, 2, 2.5, 3, 3.5, 4, 4.5, and 5 g.

46. The haemostatic kit according to any one of items 23 to 45 further comprising an outer packaging defining a sterile barrier seal for enclosing said containment unit.

47. The haemostatic kit according to any one of items 23 to 45, wherein the containment unit is sterile.

48. The haemostatic kit according to any one of items 23 to 47, wherein the containment unit-facing side of the outer packaging and the containment unit are sterile.

49. A process for preparing a haemostatic product comprising the steps of:
  i) providing a sterile containment unit having a first internal volume and at least one aperture for opening and comprising a second volume of haemostatic agent, said second volume being no more than 90% of the first volume;
  ii) adding a third volume of liquid to said containment unit; and
  iii) mixing the haemostatic agent and the liquid by shaking the containment unit.

50. The process for preparing a haemostatic product according to item 49, wherein the mixing proceeds without substantial exposure of said haemostatic agent and said liquid to an environment external to that the containment unit.

51. The process for preparing a haemostatic product according to any one of items 49 to 50, wherein the haemostatic agent is collagen or collagen-derived powder.

52. The process for preparing a haemostatic product according to item 51, wherein said collagen or collagen-derived powder comprises essentially of gelatin.

53. The process for preparing a haemostatic product according to any one of items 49 to 52, wherein said haemostatic product is in the form of a putty-like paste comprising 20 to 99% w/w of collagen.

54. The process for preparing a haemostatic product according to any one of items 49 to 53, wherein the containment unit is rigid, comprises at least one opening and one closure-unit and such that the mixing proceeds without loss of liquid.

55. The process for preparing a haemostatic product according to any one of items 49 to 54, wherein said second volume is less than 85% of the first volume, preferably less than 80%, even more preferably less than 75% of the first volume, such as 70%, 65% or 60% of the first volume.

56. The process for preparing a haemostatic product according to item 49 comprising the steps of:
 i) providing a containment unit having a first internal volume and at least one aperture for opening said aperture closed by a closure-unit and comprising a second volume of haemostatic agent, said second volume being no more than 90% of the first volume;
 ii) adding a third volume of liquid to said containment unit; and
 iii) mixing the haemostatic agent and the liquid by shaking the containment unit.

57. The process for preparing a haemostatic product according to item 49 wherein the sterile containment unit is further comprises an outer packaging defining a sterile barrier seal for enclosing said containment unit.

58. The process according to item 57, wherein the containment unit comprises a surface which makes at least partial contact with the outer packaging the containment-unit contacting side is sterile.

59. A method of promoting haemostatis comprising administering an effective amount of a putty-like paste comprising 20 to 33% w/w of collagen to a patient in need of haemostatis, wherein the putty-like paste is prepared according process defined in to any one items 49 to 58.

60. Use of a containment unit defining a first internal volume and second volume of collagen or collagen-derived powder for the preparation of a haemostatic kit wherein the second volume is less than 90% of the first volume.

The invention claimed is:

1. A medical device for preparing a haemostatic paste, consisting of:
 i) a containment unit defining a first internal volume and being comprised of a material impermeable to a fluid, wherein the containment unit further comprises an opening to an external environment and a closure-unit for closing the opening,
  wherein the opening is re-closable with the at least one closure-unit, and
 ii) a sterile haemostatic agent in powder form contained in said containment unit and having a second volume of less than 90% of the first internal volume of the containment unit;
  wherein said sterile haemostatic agent is capable of forming a putty-like paste in the presence of a third volume of liquid; and
 iii) an outer packaging defining a sterile barrier seal enclosing said containment unit;
  wherein the remaining volume of at least 10% of the internal volume is a void volume allowing for the addition of a third volume of liquid from an external environment to the sterile haemostatic agent in powder form through the opening and mixing of the sterile haemostatic agent in powder form and the added liquid within the containment unit without present exposure to an environment external to that of the containment unit.

2. The medical device according to claim 1, wherein the at least one opening is separated from said external environment by the closure-unit during the mixing.

3. The medical device according to claim 1, wherein said haemostatic agent in powder form is gelatine.

4. The medical device according claim 1, wherein said haemostatic agent in powder form is collagen.

5. The medical device according to claim 1, wherein the volume of said haemostatic agent is less than 80% of the internal volume of the containment unit.

6. The medical device according to claim 1, wherein said haemostatic agent is provided in an amount from about 0.5 to 5 g.

7. The medical device according to claim 1, wherein the haemostatic agent is provided in an amount of about 1 g, and the volume of the containment unit is 50 to 100 cubic centimetres.

8. The medical device according to claim 1, wherein said containment unit is rigid or semi-rigid and comprises a wide-mouth opening.

9. The medical device according to claim 8, wherein said containment unit and closure unit is made of a material selected from the group of polypropylene, polyethylene, PVC and PET.

10. The medical device according to claim 9, wherein the containment unit is made from substantially rigid polyethylene or polypropylene, and has a single opening which may be sealed with a threaded, polyethylene or polypropylene closure.

11. The medical device according to claim 1, wherein said outer packaging comprises a laminated foil pouch.

12. A haemostatic kit comprising
 i) the medical device according to claim 1, and
 ii) a third volume of a sterile liquid in a second containment unit whose internal volume is physically separated from the containment unit of the medical device,
 wherein the kit is suitable for adding said liquid to said containment unit of the medical device.

13. The haemostatic kit according to claim 12, wherein said third volume of liquid is selected from the group of water, an aqueous solution, saline, an aqueous solution comprising an isotonicity-adjusting agent, an aqueous solution comprising thrombin and/or an aqueous solution comprising a bacteriostatic agent.

14. A process for preparing a haemostatic paste comprising the steps of:
 A) removing the outer packaging of the medical device according to claim 1,
 B) opening the containment unit to the external environment,
 C) adding a sterile liquid to said containment unit,
 D) re-closing the at least one opening of the containment unit by the closure-unit, and
 E) mixing the liquid and the sterile haemostatic agent contained in the containment unit without substantial exposure of said haemostatic agent and said liquid to an environment external to the containment unit, thereby preparing the haemostatic paste.

15. The process according to claim 14, wherein said sterile liquid of step C) is added by pouring the liquid through the at least one opening of the containment unit.

16. The process according to claim 14, wherein said mixing of step E) is performed by shaking the containment unit.

17. The process according to claim 14, wherein the containment unit is transferred into a sterile field before opening said containment unit in step B).

18. The process according to claim 14, wherein the sterile liquid of step C) is added in a volume less than 35% of the second volume of haemostatic agent.

19. The process according to claim 14, wherein the haemostatic paste of step E) is a putty-like paste.

* * * * *